United States Patent [19]

Misko et al.

[11] Patent Number: 5,380,336

[45] Date of Patent: Jan. 10, 1995

[54] METHOD AND APPARATUS FOR STEREOTACTIC RADIOSURGERY AND FRACTIONATED RADIATION THERAPY

[75] Inventors: John Misko, 3190 SW. Fairmount Rd., Portland, Oreg. 97201; Robert J. Miller, Sherwood, Oreg.; Stan Heard, Portland, Oreg.

[73] Assignee: John Misko, Portland, Oreg.

[21] Appl. No.: 48,384

[22] Filed: Apr. 16, 1993

[51] Int. Cl.6 .................................. A61B 17/00
[52] U.S. Cl. ........................... 606/130; 128/898
[58] Field of Search ............... 606/1, 130; 604/116; 128/898, 653.1–653.5

[56] References Cited

U.S. PATENT DOCUMENTS

| | | |
|---|---|---|
| 3,357,431 | 12/1967 | Newell . |
| 3,460,537 | 8/1969 | Zeis . |
| 4,341,220 | 7/1982 | Perry ................................ 128/630 |
| 4,350,159 | 9/1982 | Gouda . |
| 4,397,307 | 8/1983 | Keller ............................... 606/130 |
| 4,463,758 | 8/1984 | Patil et al. . |
| 4,501,009 | 2/1985 | Abele ................................ 378/19 |
| 4,592,352 | 6/1986 | Patil . |
| 4,608,977 | 9/1986 | Brown . |
| 4,617,925 | 10/1986 | Laitinen . |
| 4,627,420 | 12/1986 | Katz . |
| 4,638,798 | 1/1987 | Shelden . |
| 4,706,665 | 11/1987 | Gouda . |
| 4,750,487 | 6/1988 | Zanetti . |
| 4,791,934 | 12/1988 | Brunnett . |
| 4,805,615 | 2/1989 | Carol . |
| 4,827,491 | 5/1989 | Barish ............................... 378/65 |
| 4,869,247 | 9/1989 | Howard . |
| 4,923,459 | 5/1990 | Nambu .............................. 606/130 |
| 4,930,143 | 5/1990 | Lundgren .......................... 378/37 |
| 4,955,891 | 9/1990 | Carol ................................. 606/130 |
| 4,998,938 | 3/1991 | Ghajar et al. .................... 606/130 |
| 5,027,818 | 7/1991 | Bova et al. . |
| 5,037,374 | 8/1991 | Carol ................................. 600/1 |
| 5,047,036 | 9/1991 | Koutrouvelis .................... 606/130 |
| 5,078,140 | 1/1992 | Kwob . |
| 5,099,208 | 3/1992 | Fitzpatrick ........................ 324/312 |
| 5,099,846 | 3/1992 | Hardy . |
| 5,116,345 | 5/1992 | Jewell ............................... 606/130 |
| 5,125,888 | 6/1992 | Howard ............................ 600/12 |
| 5,143,076 | 9/1992 | Hardy . |
| 5,160,337 | 11/1992 | Cosman ............................ 606/130 |
| 5,163,430 | 11/1992 | Carol . |
| 5,176,689 | 1/1993 | Hardy ............................... 606/130 |
| 5,207,688 | 5/1993 | Carol ................................. 606/130 |

OTHER PUBLICATIONS

*Radiotherapy Applications & Developments, Physicians' Series*, Jul., 1991, (4 pages).

*Primary Examiner*—Stephen C. Pellegrino
*Assistant Examiner*—Glenn K. Dawson
*Attorney, Agent, or Firm*—Alan T. McCollom

[57] ABSTRACT

The invention includes a rigid frame that is positioned around the skull to define a multi-dimensional coordinate system. Multiple arms are coupled to the frame, each arm having an attachment assembly movable along a longitudinal axis directed toward the center of the rigid frame assembly. Multiple receptors are either attached to the skull or drilled into the skull for receiving an associated attachment assembly. The receptors provide a mounting base upon which the frame is repeatedly attached and detached from the skull at the same reproducible reference location. Each arm has a multi-station receptacle that receives various attachments used for mounting and attaching the receptors. Special bushings are used to lock the attachment assembly in a preset longitudinal position in relation to the arm. The locked attachment assembly can then be removed from the arm allowing the frame to be removed from the skull while maintaining frame position information.

7 Claims, 8 Drawing Sheets

METHOD AND APPARATUS FOR STEREOTACTIC RADIOSURGERY AND FRACTIONATED RADIATION THERAPY

BACKGROUND OF THE INVENTION

This invention relates generally to equipment for performing stereotactic radiosurgery and more particularly to art apparatus that can be detached and reattached at the same location on a skull to provide a reproducible three-dimensional reference when locating and radiating intracranial and head and neck lesions.

Stereotactic radiosurgery is the practice of gaining precise access to a specific point in the cranium through the application of an external three-dimensional coordinate system. A conventional stereotactic system utilizes a brain mapping technique such as computerized tomographic (CT) scanning or magnetic resonance imaging (MRI), to produce an image representing a "slice" of brain tissue. A series of "slices" constitute a complete study and represent a three-dimensional picture of the brain that defines the relationship of neurological structures and accurately localizes lesions.

The CT or MRI scanning equipment is used in coordination with a frame mounted to a patient's skull by pins or screws. The frame provides a reference that defines the multi-dimensional coordinate system used in identifying intracranial and head and neck lesions. After being attached to the patient's skull, the frame is attached to a platform within the scanning equipment. The frame keeps the skull in the same position during the lesion localization process. The frame remains attached to the patient's skull after localization and through stereotactic radiosurgery to keep the skull in the same relative position in relation to the frame reference points.

There are various surgical and radiosurgical procedures performed on lesions after their localization inside the skull. For example, U.S. Pat. No. 5,027,818 to Bova et. al. describes a radiosurgical method for destroying lesions by directing a radiation beam into the skull. Bova uses a stereotactic frame to assist in localizing the target (e.g., lesion) inside the skull. The intracranial target is then positioned at the focal point of the radiation beam. Multiple radiation pathways are then taken through different areas of the brain all traveling though the same target focal point. Since each radiation pathway is through a different area of the brain, the amount of radiation applied to healthy brain tissue is minimal. At the focal point (i.e., lesion location), however, a very sizable radiation dose is delivered which can, in certain cases, lead to obliteration of the lesion.

The radiosurgical process, in some instances, is a much safer treatment option than conventional surgical methods. It is especially important, however, that the radiation is minimized on certain critical structures inside the skull. For example, when using radiation treatment on a patient's brain, it is important that a minimum radiation dosage be applied to the patient's optic nerves. Therefore, before radiation treatment, the physician must carefully decide on each path the radiation beam will travel through the brain to reach target area. To maintain the same skull reference location, the frame must remain tightly fastened to the skull while the physician is planning this radiosurgical strategy.

To prevent damage to healthy tissue, it would be preferable to apply lower doses of radiation to the lesion over multiple radiation sessions (i.e, fractionated stereotactic radiation therapy). Fractionareal stereotactic radiation therapy, however, is prohibitively expensive and time consuming since the frame must be reattached, and the lesion relocalized before each radiation therapy session. Fractionated stereotactic radiation therapy would be less expensive if the same lesion coordinates could be used for each therapy session. To use the same coordinates for each therapy session, the frame would have to be attached to the skull in the same position in relation to the skull. Present stereotactic immobilization devices or frames, however, cannot be reattached to the skull in the same location with acceptable accuracy. Therefore, the lesion must be relocalized before each radiosurgical session or the radiation beam may have a focal point that is no longer centered on the lesion. An off-target focal point could damage healthy tissue and critical structures in the brain.

The stereotactic frame, while necessary to accurately identify the intracranial target, is time-consuming to attach and is burdensome to carry while attached to a patients skull. For example, correctly fastening the frame to the skull can take one to several hours. Therefore, it is prohibitively expensive to reattach the frame before each radiation therapy session. By necessity, the frame is also large and rather bulky. The large frame is necessary to securely mount the skull to the radiosurgical equipment. Since radiation therapy sessions that are typically performed once a day and continue for several weeks, it is impractical for a patient to carry the frame around on his head throughout the entire radiation therapy process.

To reduce the time and cost of radiation therapy, a single radiation treatment technique or "one-shot" is performed that directs an intense radiation beam at the lesion. This "one-shot" technique in some situations, however, does not destroy a lesion as effectively as fractionated radiation therapy. The high intensity radiation beam also has a greater tendency to damage healthy tissue while traveling through the brain to the lesion. If the lesion is located in certain cranial areas, there is no way to destroy the lesion without also damaging some critical brain structures. Even if a "one-shot" radiation treatment were feasible, the patient must still wear the frame while the physician is localizing the target and deciding upon the various paths the radiation beam will travel to the lesion focal point. During this localization period, the frame applies extreme pressure on the skull. The pressure of the frame is uncomfortable and may cause severe headaches. Thus, regardless of whether fractionated radiation therapy or a "one-shot" radiosurgery process is utilized, it would be beneficial to be able to detach the frame from the patient's skull between the various steps of the stereotactic radiosurgery process.

There are several stereotactic frames used in locating intracranial lesions. However, present frames cannot be attached and reattached to a skull at a reproducible reference location. For example, U.S. Pat. No. 3,357,431 to Newell describes an apparatus fixed to a cranium via screws mounted into the skull. The apparatus in Newell, however, is not used as a three-dimensional reference for CT scanning and only provides a mounting platform for invasive surgical equipment. In addition, the frame of Newell cannot be repeatedly attached to the skull at the same reference position. U.S. Pat. No. 5,176,689 to Hardy et. al. and U.S. Pat. No. 4,923,459 to Nambu, describe apparatus that are attached to the skull to determine the location and size of tumors. However, the apparatus in Hardy and Nambu also can not be detached and accurately reattached to the skull at the same reference location. Therefore, the apparatus described in Newell, Hardy, and Nambu are not useful in solving the problems of time and cost that presently exist with localizing lesions before preforming stereotactic surgical procedures.

SUMMARY OF THE INVENTION

It is, therefore, an object of the invention to reduce the time and cost of localizing intracranial targets before each fractionated stereotactic radiation therapy session.

Another object of the invention is to increase the accuracy in reattaching a stereotactic frame to a skull at the same reference location in relation to the skull.

A further object of the invention is to increase the variety of stereotactic radiosurgical procedures that can be performed on a patient.

The invention is a system for performing stereotactic radiosurgical procedures upon a target within a skull. The system comprises a rigid frame that is positioned around the skull to define a multi-dimensional coordinate system. Multiple arms are coupled to the frame, each arm having an attachment assembly that is movable along a longitudinal axis directed substantially toward the center of the rigid frame assembly. Multiple receptors are either attached to the skull or drilled into the skull for receiving an associated attachment assembly. The receptors provide a mounting base upon which the frame can be repeatedly attached and detached from the skull at the same reproducible reference location.

A drill and tap are slidably attachable to any one of the arms along the same longitudinal axis as the associated attachment assembly. The drill is used for drilling a bore in the skull at each receptor location and the tap is used to form an internal screw thread in such a bore. An insertion mechanism is then slidably attached to the arms to insert a receptor into the bore.

Each arm has a multi-station receptacle that receives the various attachments used for mounting and attaching the receptors. Special bushings are insertable inside the arm receptacles to hold the skull mounting devices along a single mounting axis substantially perpendicular with the longitudinal axis of the associated arm. A locking mechanism is used to lock the attachment assembly in a preset longitudinal position in relation to the arm. The locked attachment assembly can then be removed from the arm allowing the frame to be removed from the skull while maintaining frame position information.

The invention is used in stereotactic radiosurgery processes in the following manner. The stereotactic frame is first attached to the skull and holes drilled at the locations where the frame mounts to the skull. Receptors are then installed into the skull holes and the frame reattached to the receptors thereby locating it about the skull at a given reference position. The lesion is then localized according to the frame reference position and a stereotactic radiosurgical procedure performed. After the stereotactic radiosurgical procedure, the frame is removed leaving the receptors attached in the skull holes. Before the next stereotactic surgical procedure, the frame is reattached in the receptors at the same reference position. Alternatively, the holes drilled in the skull are used as receptors and the frame attached directly into the drilled holes.

The lesion is localized by deriving a set of coordinates relative to the frame reference position. Since the frame is reattached to the skull in the same position, the same lesion coordinates are used For each subsequent stereotactic radiosurgical procedure. Having the capability to reuse the same lesion coordinates allow subsequent radiosurgical procedures to be performed without having to completely relocalize the lesion. Thus, the cost and time of each therapy session is reduced.

The foregoing and other objects, features and advantages of the invention will become more readily apparent from the following detailed description of a preferred embodiment of the invention which proceeds with reference to the accompanying drawings.

DETAILED DESCRIPTION

Figure 1:
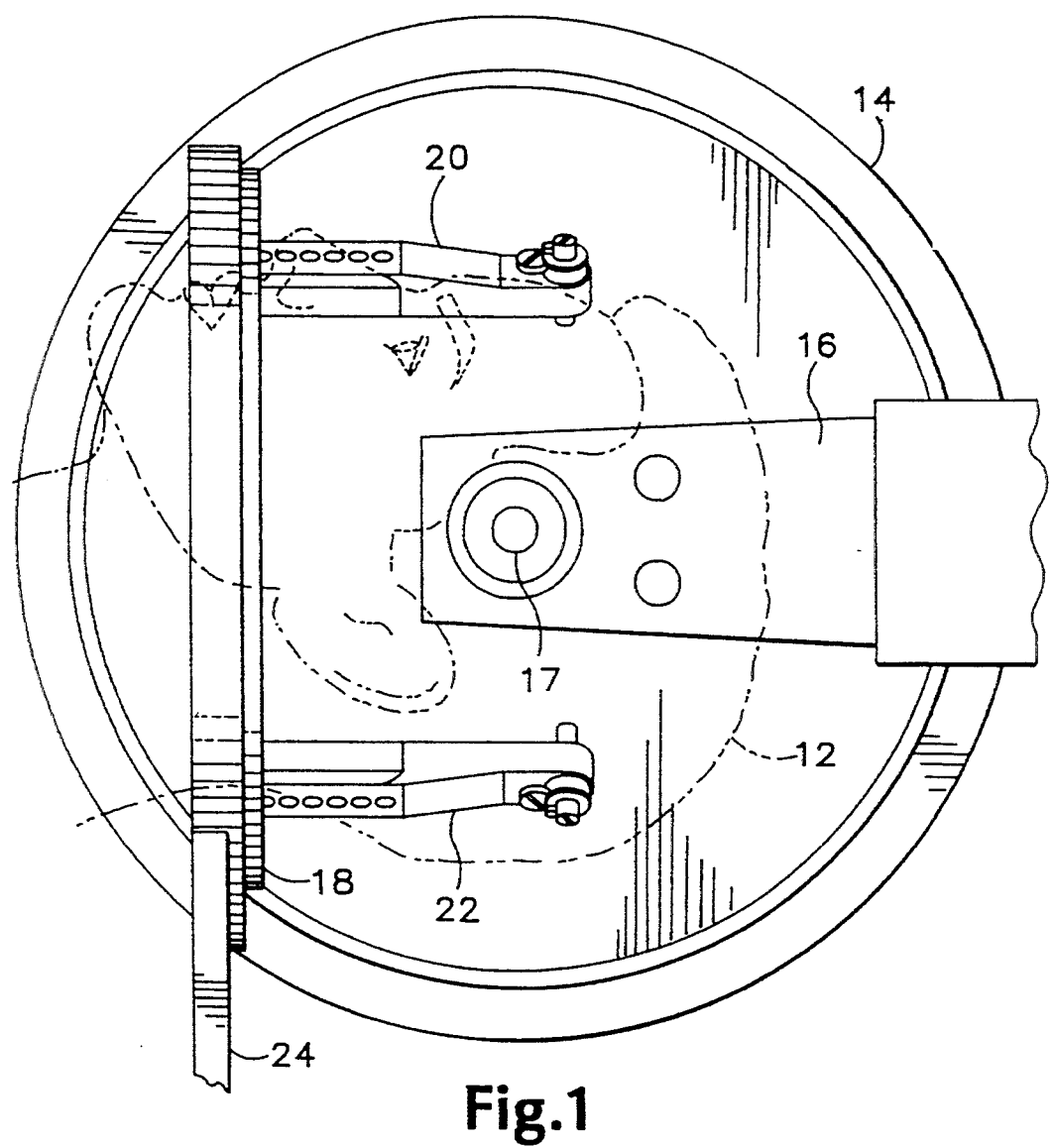
FIG. 1 is a side view of a stereotactic frame according to the invention attached to conventional radiation apparatus which may be employed for stereotactic radiosurgery.

FIG. 1 is a side view of a stereotactic frame 18 according to the invention attached to a gantry 14 of a conventional radiation apparatus, such as a linear accelerator. The preferred embodiment of the invention is shown and described herein in conjunction with a linear accelerator. The method and apparatus of the present invention can be equally well implemented with several brain mapping techniques for localizing and defining targets such as angiography, CT scanning, MRI (magnetic resonance imaging) and PET (positron emission tomography). The linear accelerator in FIG. 1 is used for stereotactic radiosurgery and fractionated radiation therapy on intracranial lesions inside a skull 12. A collimator 17 is attached by a support arm 16 to the gantry 14. The gantry 14 carries the radiation-emitting collimator 17 in an arc around the skull 12. The frame 18 (ring) has a circular outside surface that mounts inside a circular bracket 24. In the present embodiment of the invention, ring 18 is commercially available. Bracket 24 is attached to a floor-stand (not shown). Arms 20 and 22 attach the ring 18 to the skull 12.

Stereotactic radiosurgery procedures for identifying and destroying inner cranial lesions, are well known to those skilled in the art and, therefore, will not be described in detail. A specific procedure and apparatus for performing stereotactic radiosurgery is described in U.S. Pat. No. 5,027,818 to Bova and is hereby incorporated by reference.

The first step in the stereotactic radiosurgery process is localization of the lesion (e.g., tumor). One method of localization is CT and involves fitting the skull 12 inside a stereotactic frame 18 as illustrated in FIG. 1. A stereotactic localizing device is then attached to the frame. The subsequent brain mapping and target definition produces precise, x, y, z, coordinates of the target (to an accuracy of less than ½ millimeter) relative to the stereotactic frame.

The patient is aligned in tire gantry 14 and contiguous slices, beginning at the level of the ring 18 and advancing superiorly past the top of the patient's skull 12, are obtained. If the target volume is identified in the computerized tomography image, the x, y, z, coordinates of the target volume are again recalculated to provide a double check of the x, y, z, coordinates previously derived relative to the stereotactic ring 18. The CT scan provides three dimensional anatomical information of the patient that allows a solid patient model to be constructed.

The data from the CT scan, anglographic films and/or MRI is then transferred to a commercially available dosimetry computer system (not shown). For high single fractions of radiation to be delivered to the target volume, the radiation source emitted from collimator 17 is mixed through multiple arcs around the skull 12. For the radiotherapist and neurosurgeon to be able to examine the consequence of each portion of the arc prior to radiating; the patient, the dosimetry system displays each are segment on a computer screen. If any particular arc results in an extensive dose of radiation to a critical structure inside the brain, the therapist alters the are parameters to avoid the anatomical area of concern. Once the acceptable radiation treatment scheme has been derived, the coordinates of the isocenter (focal point of the radiation beam), the collimator coordinates, and the arc parameters are transferred to the radiation apparatus 14 and the radiation administered to the patient.

As explained above, the target coordinates are generated relative to the frame 18. Therefore, moving the ring 18 in relation to the skull 12 would cause the radiation beam focal point to be misaligned with the target location. To prevent focal point misalignment, conventional stereotactic rings are kept on during the entire localization process. In addition, due to the extensive time requirements required for all of the localization procedures described above, fractionated stereotactic radiation therapy is not extensively performed.

In the present invention, however, the arms 20 and 22 can be detached from the skull 12 and reattached to the skull 12 at the same reference location. This repeatable positioning of ring 18 at the same x, y, z coordinates in relation to the skull allow the radiation apparatus 14 to use the same coordinates for each radiation therapy session. The ring 18 can also be removed between various localization procedures, for example, while the physician computes and optimizes radiation doses.

Figure 2:
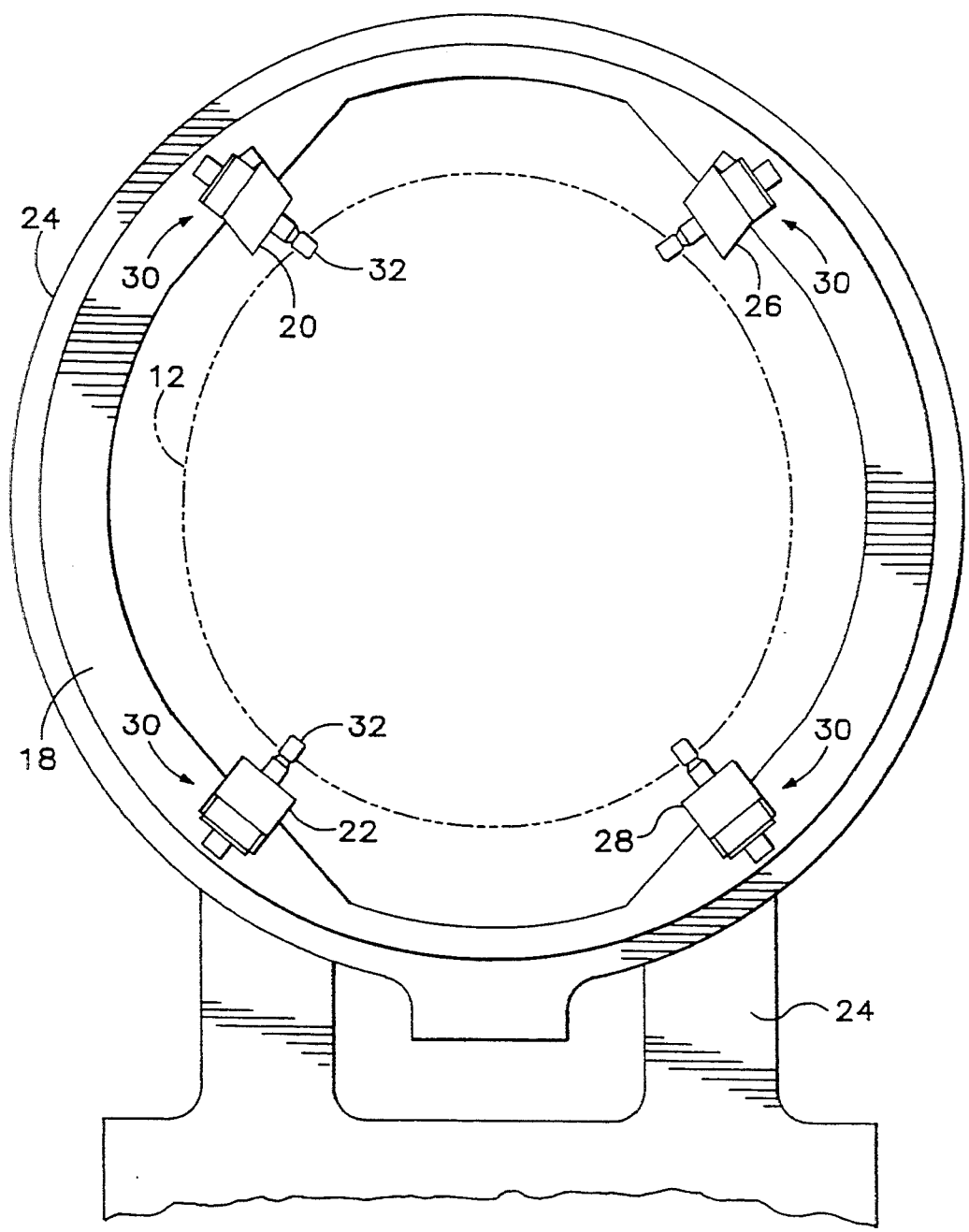
FIG. 2 is a front view of the stereotactic frame shown in FIG. 1.

To explain further, FIG. 2 shows a front view of the stereotactic ring 18 shown in FIG. 1. The ring 18 is seated inside the bracket 24 and has four arms 20, 22, 26, and 28 extending along a longitudinal axis substantially parallel with the center axis of the ring 18. Each arm is attached to the skull 12 by an attachment assembly 30. The attachment assembly sits in a receptor 32 residing in the skull 12. The arms are positioned so that the attachment assembly 30 contacts with skull 12 in a direction substantially perpendicular with the tangential plane passing through the skull contact point.

For example, front arms 20 and 26 are angled toward each other slightly more than rear arms 22 and 28 to account for the inclined surfaces on the front of skull 12. The rear arms 22 and 28 are less angled to provide perpendicular contact with the substantially round surface at the back of skull 12. The perpendicular contact of each attachment assembly 30 allows a maximum amount of skull bone to surround each receptor 32. By maximizing the amount of skull bone surrounding each receptor, the stability in which the receptor 32 is seated in the skull is increased. As will later be more fully described, the arms are detachable from ring 18. This feature permits attachment of the two types of arms, arms 20, 26, on the one hand, and arms 28, 30, to different locations on the ring to accommodate differently shaped skulls. Similarly, different numbers of each type of arm may be used up to and including all of the arms being of one type or the other.

The receptors provide a stable mounting foundation for each attachment assembly 30 and allow the ring 18 to be attached and detached from the skull at a reproducible reference location. For example, the attachment assembly 30 is removable from the frame arm to allow the ring 18 to be removed from the skull 12. However, keeping the receptors 32 in the skull allow each attachment assembly 30 to be reseated in an associated receptor 32 at the previously defined reference location. Thus, the ring 18 can be repeatably repositioned in the same location in relation to the skull 12. A series of skull processing procedures are performed on skull 12 before inserting receptors 32 and are described in detail below.

Figure 3:
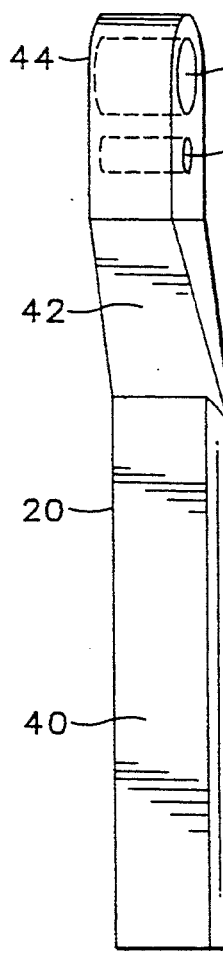
FIG. 3 is an enlarged side view of a front arm for the stereotactic frame shown in FIG. 1.
Figure 4:
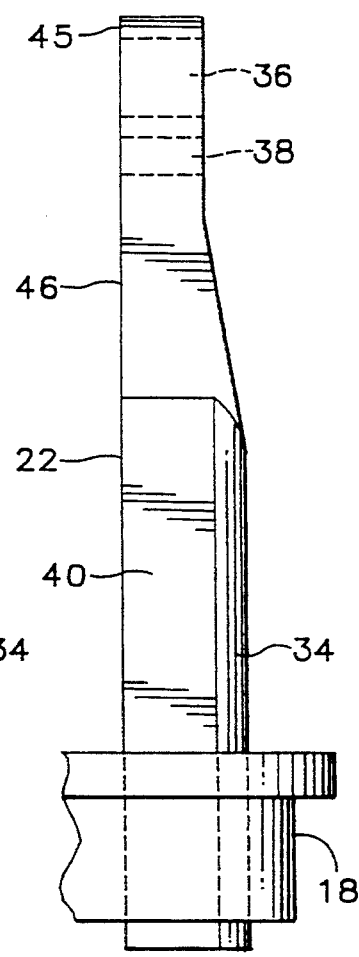
FIG. 4 is an enlarged side view of a rear arm for the stereotactic frame shown in FIG. 1.

FIG. 3 is a side view of the front arm 20 and FIG. 4 is a side view of the rear arm 22 shown in FIG. 1. Both the front and rear arms have a shaft 40 with oppositely inclining sides 34. The front arm 20 has a rotated assembly section 44 that is skewed in relation to the shaft 40. In FIG. 4, the assembly section 45 is aligned with shaft 40. Both the front and back arms have equal diameter bushing holes 36 and equal diameter lock screw holes 38. The shaft 40 of rear arm 22 is shown inserted into the ring 18.

Figure 5:
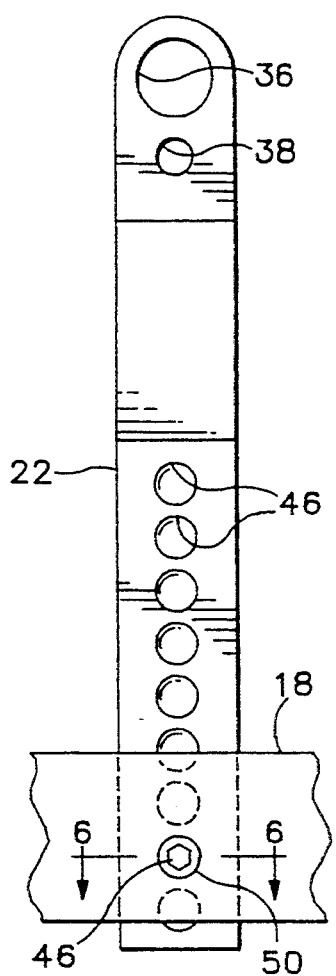
FIG. 5 is an enlarged front view of the rear arm shown in FIG. 4.
Figure 6:
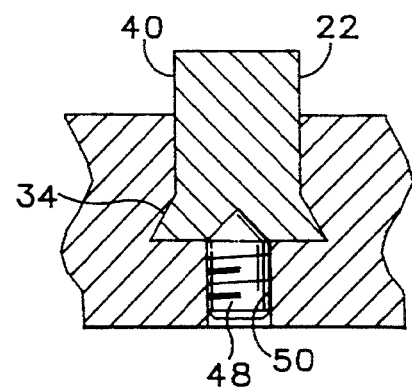
FIG. 6 is a view taken along line 6—6 in FIG. 5.

FIG. 5 is a front view of the rear arm 22 shown in FIG. 4. The shaft of each front and back arm has a set of female conical bores 46 for receiving a screw 48 through a hole in ring 18. FIG. 6 is a cross-section of the ring 18 and arm 22 shown in FIG. 5. A dovetail slot in ring 18 receives the shaft 40 of arm 22. The appropriate conical bore 46 (FIG. 5) is aligned with the ring hole 50 according to the size of the patient's skull and lesion location. Ring hole 50 has internal threads that interlock with the threads of screw 48. Thus, rotating screw 48 into hole 50 forces the conical tip of screw 48 against the conical bore 46. The tip of screw 48 forces shaft 40 against the back face of the dovetail slot holding arm 22 securely in the ring 18.

Figure 7:
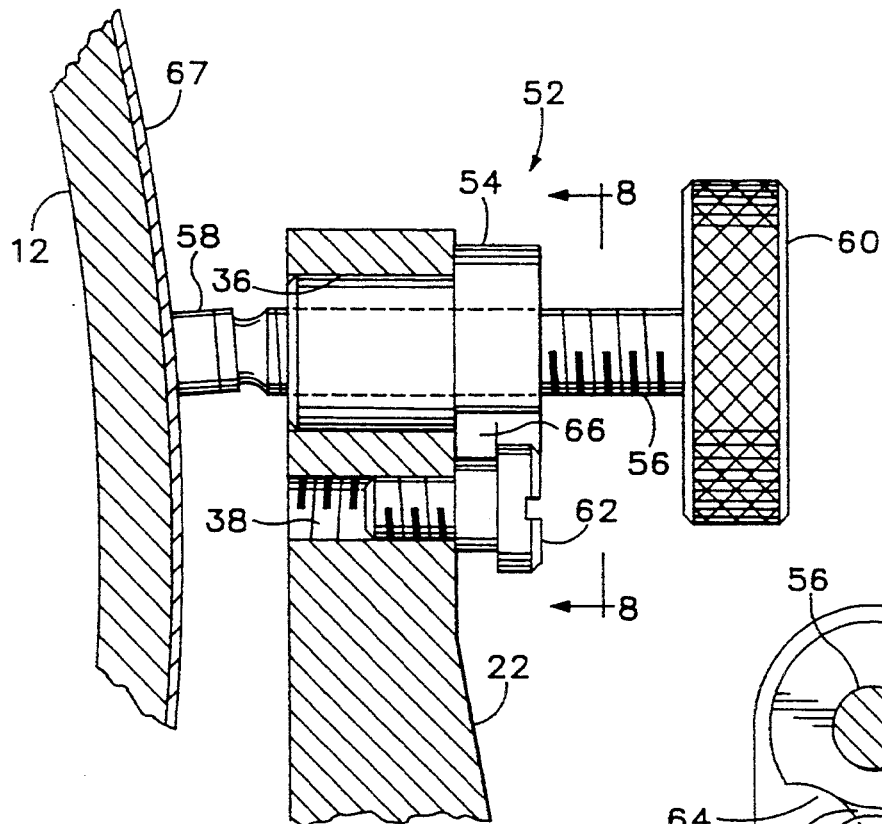
FIG. 7 is a cross-sectional side view of a clamp assembly.
Figure 8:
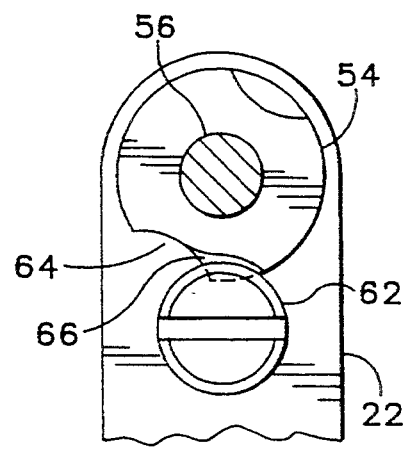
FIG. 8 is a view taken along line 8—8 in FIG. 7.

FIG. 7 is a side view of a clamp assembly 52 and FIG. 8 is a view taken along line 8—8 in FIG. 7. A clamp bushing 54 is insertable inside hole 36 (see FIG. 5). The bushing 54 has an internal threaded hole that receives and interlocks with the threads of clamp shaft 56. The front end of clamp shaft 56 is coupled to a swiveled clamping mount 58 and the rear end of clamp shaft 56 is attached to a crank 60. The bushing 54 is locked to the arm 22 by a lock screw 62. The threads of lock screw 62 engage with the internal threads of hole 38 (see FIG. 5) and hold a flange 66 on bushing 54 against the rear face of arm 22. Lock screw 62 allows quick insertion and extraction of various bushings from hole 36, however, alternative attachment mechanisms could also be used to attach various apparatus to arm 22.

The clamp assembly 52 is used to initially attach the ring 18 and arms 20, 22, 26, and 28 to the skull 12 and is installed by inserting bushing 54 into hole 36. A slot 64 in bushing 54 (FIG. 8) is positioned to pass around lock screw 62. Bushing 54 is then rotated so that flange 66 slides underneath lock screw 62. Lock screw 62 is then screwed further into hole 38 pressing against the flange 66 and holding the bushing 54 firmly against arm 22.

Rotating crank 60 moves crank rod 56 forward pushing mount 58 against skin 67 of skull 12. The mount 58 swivels slightly as it presses against the skull 12 so that the front face of mount 58 lies flat against the skull. Each of the four attachment assemblies (i.e., one for each arm) are tightened until the frame is securely fastened to the skull 12. The clamp assembly 52 is removed from arm 22 by unscrewing lock screw 62 and rotating flange 66 out from under lock screw 62. Notch 64 is then centered about lock screw 62 and bushing 54 removed from hole 36. The clamp assembly 52 shown in FIG. 7 is identical for each frame arm and provides support for the frame during the subsequent drilling and attachment processes described below.

Figure 9:
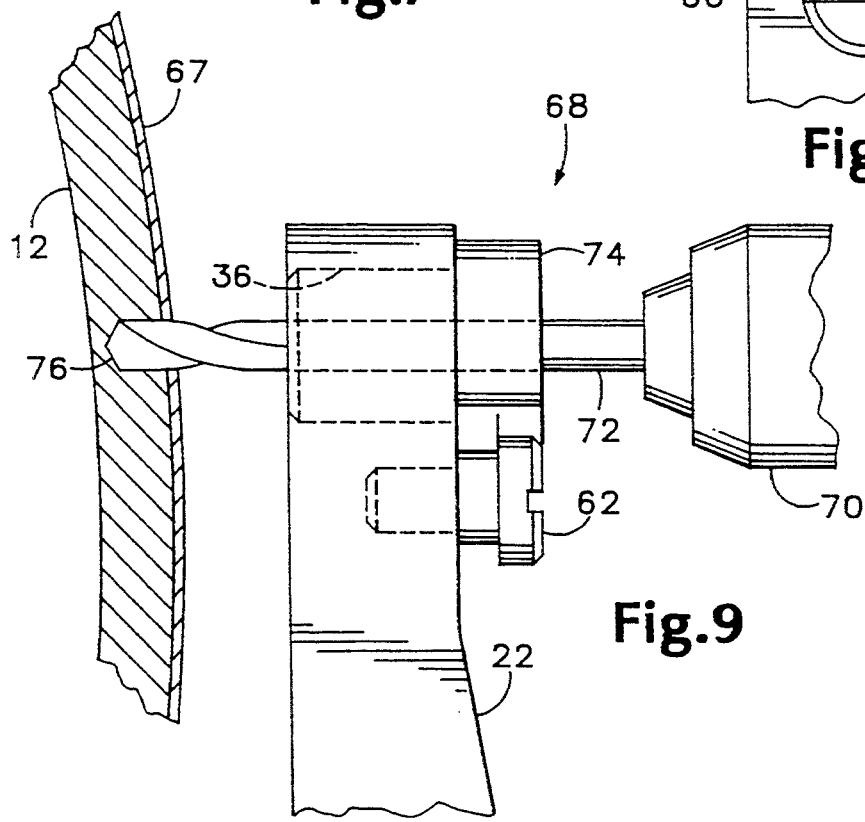
FIG. 9 is a side view of a drill assembly.

FIG. 9 is a side view of a drill assembly 68. The drill assembly includes a drill bushing 74 insertable into hole 36 of arm 22, a drill 70, and a drill bit 72. The drill bushing 74 is attached to arm 22 by lock screw 62 in the same manner as clamp assembly 52 in FIG. 7.

The drill assembly 68 is used for boring holes into skull 12. The skull holes are drilled one at a time by first removing one of tile clamp assemblies 52 as described above in FIG. 7. A drill bushing 74 is then inserted and locked into hole 36 and drill 70 enabled so that drill bit 72 begins boring a hole 76 into skull 12. After boring hole 76, drill bit 72 is removed from the skull 12 and the drill assembly 68 removed from arm 22. The drill assembly is also removed from arm 22 in the same manner as clamp assembly 52 (see FIG. 7). Various drill bits cart be utilized to create different skull holes. Different diameter drill bits require different bushings having different-sized bores therein for receiving the bit. Preferably, the clearance between the bit and the bushing hole is approximately 0.01 min. The type of holes drilled in skull 12 depend on the type of receptors inserted into the skull.

Figure 10:
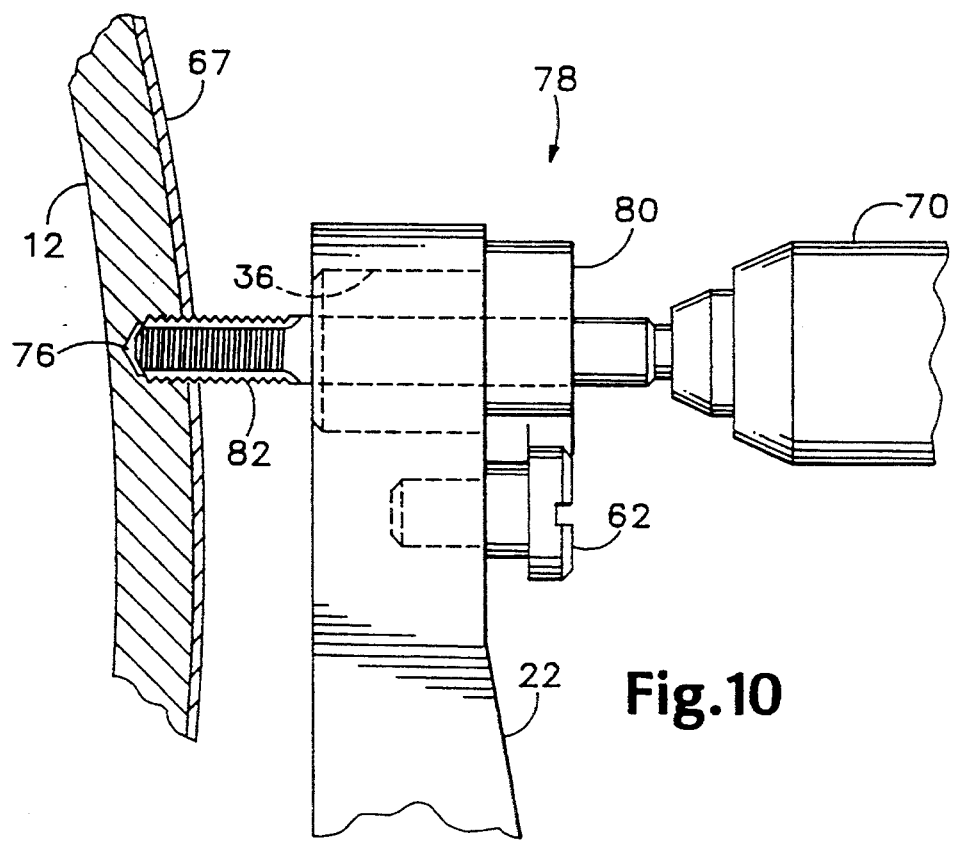
FIG. 10 is a side view of a tap assembly.

FIG. 10 is a side view of a tap assembly 78 which includes a tap bushing 80 insertable into hole 36 of arm 22. The tap bushing 80 receives a tap bit 82 that is attachable to a tap chuck 83. The tap assembly 78 is attached and detached from arm 22 in the same manner as the clamp and drill assemblies 52 and 68, respectively, as previously described above. The tap assembly is used to tap threads in the hole 76 previously drilled by drill bit 72 (FIG. 9). However, if a non-threaded receptor or a self-threading receptor is used, tap assembly 78 is not necessary.

Figure 11:
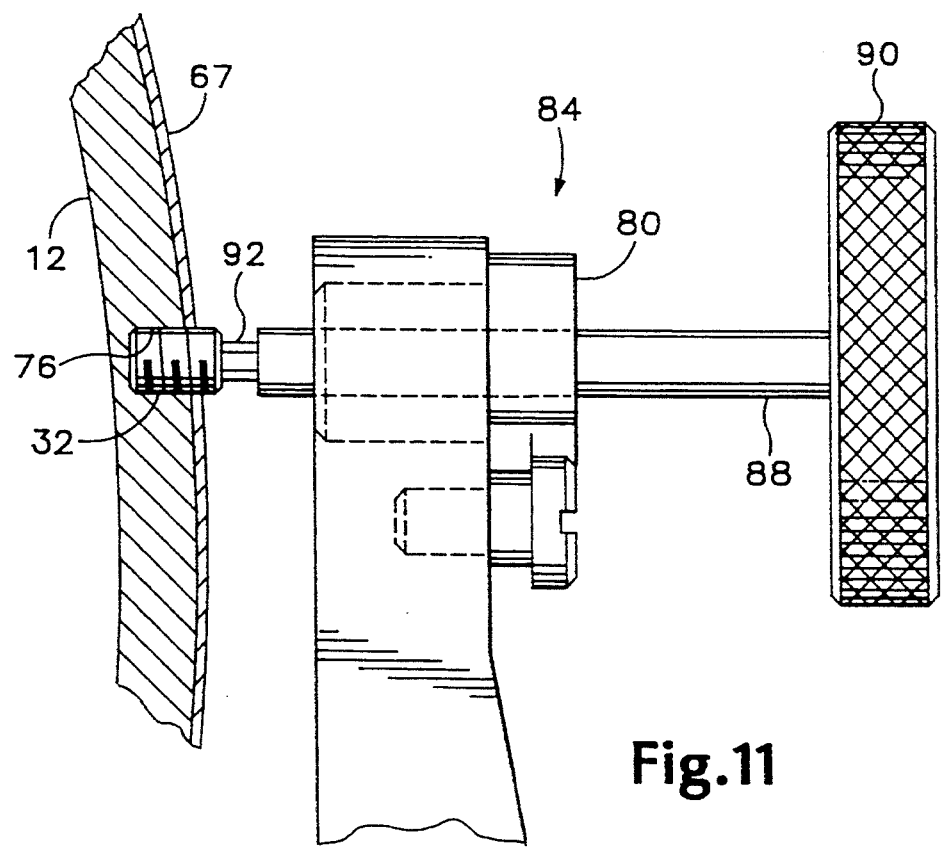
FIG. 11 is a side view of an insertion assembly.

FIG. 11 is a side view of an insertion assembly 84 which includes a shaft 88 coupled at the front end to a wrench fitting 92 and is coupled at the rear end to a crank 90. The shaft 88 is held by the same bushing 80 used in tap assembly 78 (FIG. 10). The wrench fitting 92 is insertable into an internal socket in receptor 32. After the tap bit 82 is removed from bushing 80, shaft 88 is inserted into bushing 80 and receptor 32 attached to the wrench fitting 92. Crank 90 is then rotated causing external threads on receptor 32 to interlock with the internal threads in skull hole 76. The receptor 32 is screwed tightly into hole 76 so the receptor can support frame 18.

Figure 12:
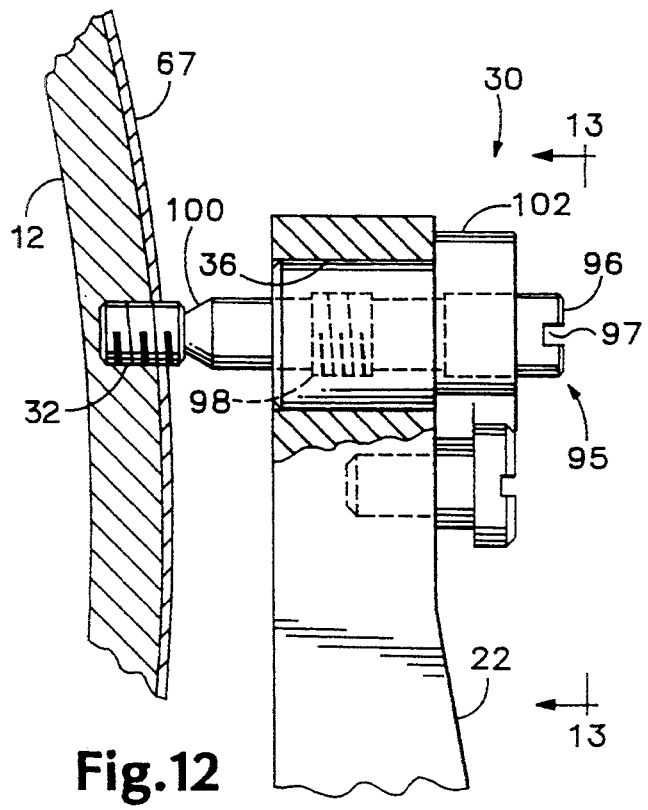
FIG. 12 is a side view of an attachment assembly.
Figure 13:
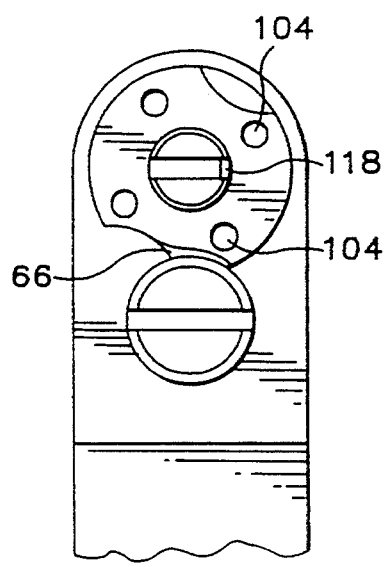
FIG. 13 is a view taken along line 13—13 in FIG. 12.

FIG. 12 is a side view of the attachment assembly 30 shown in FIG. 2 and FIG. 13 is a view taken along line 13—13 in FIG. 12. The attachment assembly includes a screw pin 95 insertable into a screw pin bushing 102. The screw pin 95 has a lockable head 96 at the rear end with a notch 97, a threaded midsection 98 that interlocks with the internal threads of the screw pin bushing 102, and a tapered tip 100 at the front end. The rear face of screw pin bushing 102 has four screw holes 104 (FIG. 13) used in coordination with a lock washer as will be described in further detail below in FIGS. 15 and 16.

The attachment assembly 30 is again inserted and extracted from arm hole 36 in the same manner as the clamp, drill, and tap assemblies. After the insertion assembly 84 (FIG. 11) is removed from arm 22, screw pin bushing 102 is inserted and locked into hole 36. Screw pin 95 is then rotated with a screw driver (not shown) into bushing 102. Bushing 102 has a close tolerance bearing bore on each end to guide the screw pin 95 repeatably regardless of the insertion distance into bushing 102. The bore on the left receives the shaft of pin 95 while the bore on the right receives head 96. Between the beating bores in bushing 102 is a threaded section which engages with external thread 98 on screw pin 95 thus allowing screw pin 95 to be driven forward. As screw pin 95 moves forward in the bushing 102, tapered tip 100 is forced into the socket of receptor 32. Screw pin 95 is sufficiently tightened against receptor 32 so that the frame 18 (FIG. 1) can not be inadvertently dismounted from the receptors or moved in relation to skull 12.

Figure 14:
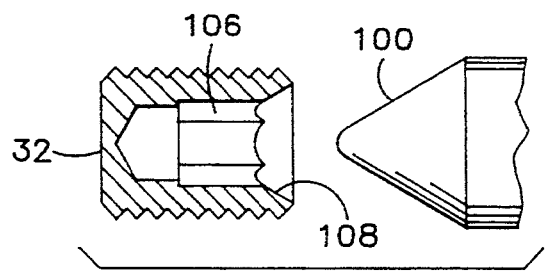
FIG. 14 is an enlarged cross-section of the receptor shown in FIG. 12.

FIG. 14 is a cross-section of the receptor 32 shown in FIG. 12. The socket inside receptor 32 comprises a wrench receiving section 106 and a screw pin receiving section 108. Section 106 is used for receiving the wrench fitting 92 of insertion assembly 84 (FIG. 11) and section 108 receives the tapered tip 100 of screw pin 95 (FIG. 12). While inserting receptor 32 in the skull (see FIG. 11), the wrench fitting 92 interlocks inside section 106, allowing the receptor to be screwed into the skull hole 76. After the receptor is securely fastened into the skull, the screw pin 95 is inserted into the receptor 32 pressing the tapered tip 100 of screw pin 95 against the interior walls of section 108.

Figure 15:
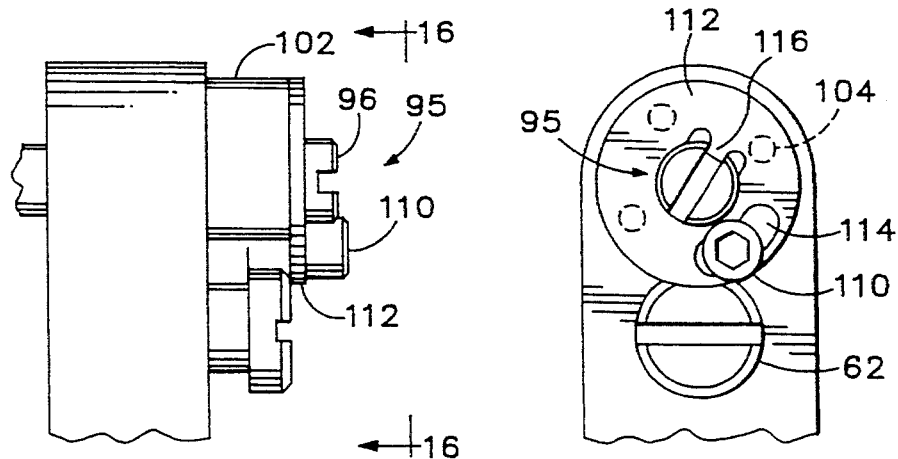
FIG. 15 is a side view of the attachment assembly in a locked position.
Figure 16:
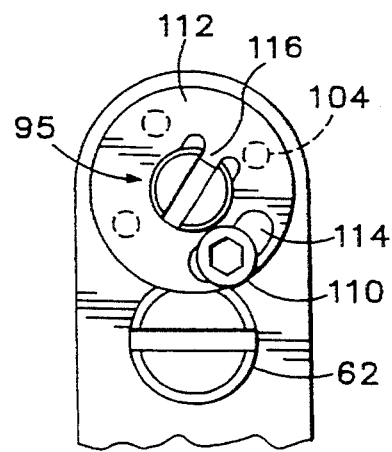
FIG. 16 is a view taken along line 16—16 in FIG. 15.

FIG. 15 is a side view of screw pin 95 locked to the screw pin bushing 102 by a lock washer 112. The lock washer 112 is held to bushing 102 by a screw 110. FIG. 16 is a front view of the lock washer 112 shown in FIG. 15. The lock washer 112 has a finger 116 that rides inside the notch 118 (in FIG. 13) in screw pin 95. Screw 110 is insertable through lock washer slot 114 into any one of the screw pin bushing holes 104.

After the screw pin 95 has been inserted sufficiently into the receptor 32 (FIG. 12), lock washer 112 is slid over the head 96 of screw pin 95 as the lock washer finger 116 tides inside screw pin notch 118. When the lock washer 112 lies flat against the rear face of bushing 102, screw 110 is inserted into the hole 104 that happens to be accessible through lock washer slot 114. If necessary, lock washer 112 can be slid off of pin 95 and turned over to place slot 114 in a location relative to one of holes 104 to permit installation of screw 110 as shown in FIG. 16. Screw 110 is then tightened clamping lock washer 112 against the rear face of bushing 102. The lock washer 112, when tightened to bushing 102 by screw 110, prevents screw pin 95 from rotating inside bushing 102. Thus, the lateral position of the arm 22 is locked at its present location which constitutes the frame reference position.

Figure 17:
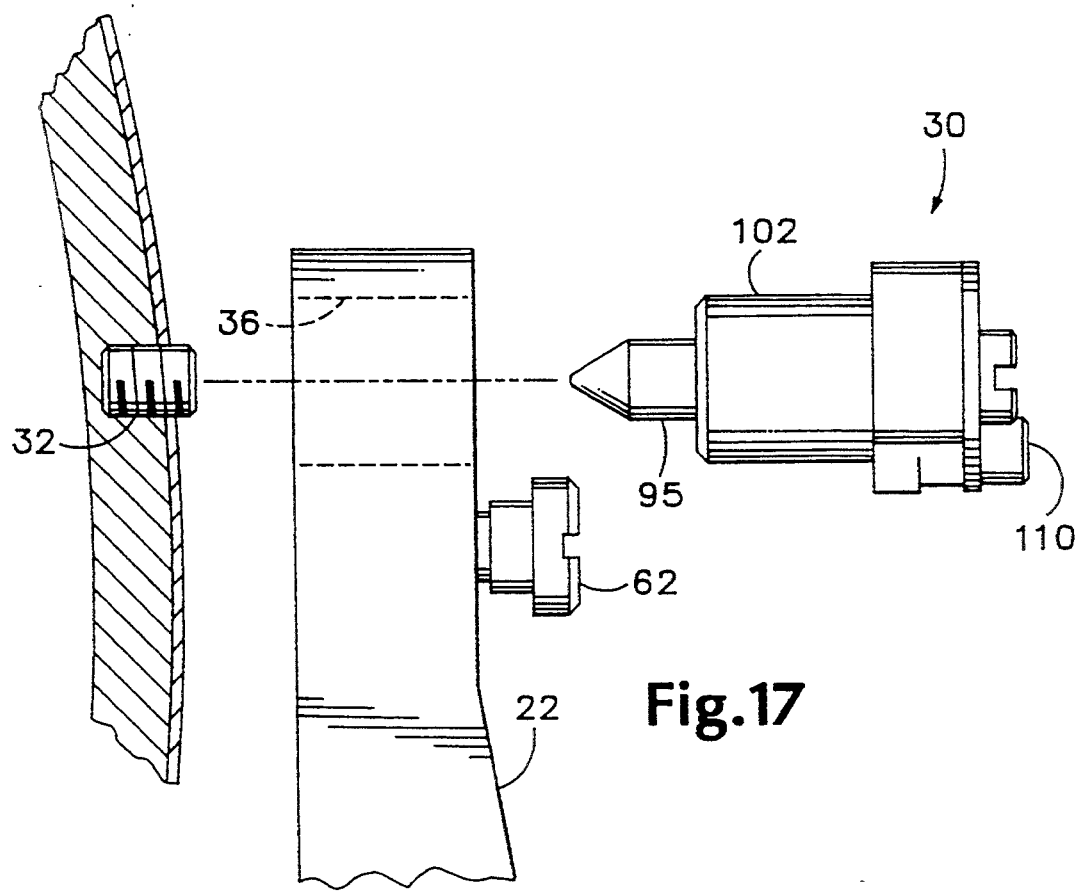
FIG. 17 is a side view of the attachment assembly shown in FIG. 15 removed from the frame arm.

FIG. 17 is a side view of the attachment assembly 30 shown in FIG. 15 removed from the frame arm 22. To remove the frame from the patients skull, the attachment assembly 30 must be removed from arm 22. However, it is necessary that the same lateral screw pin position be used when the frame is reattached to the skull 12. Therefore, the entire locked attachment assembly 30 is removed from arm 22 so that the screw pin position is maintained.

For example, to remove the frame 18 from skull 12, the screw pin bushing 102 is first removed from arm 22. Bushing 102 is removed by unscrewing lock screw 62 from arm 22 then rotating bushing 102 counter-clockwise until flange 66 no longer resides under lock screw 62. Notch 64 in bushing 102 (FIG. 8) is then centered around lock screw 62 and the bushing 102 extracted from arm hole 36. The attachment assemblies for the remaining three arms 20, 26, and 30 are removed in the same fashion. The frame is then lifted up over the skull 12.

It is important to note that the attachment assembly 30 remains in the locked position shown in FIG. 17 throughout the stereotactic radiosurgery process. Thus, the lateral position of frame 18 in relation to skull 12 remains intact. In addition, the longitudinal and latitudinal positions of the frame in relation to the skull are preserved by the receptors 32 that remain attached in the skull in between radiation sessions. Thus, the same frame position in relation to the skull 12 can be repeatably obtained by reinsetting the locked attachment assemblies 30 back into the associated arms and reclamping the screw pin bushing 102 with the lock screw 62. As long as the attachment assembly remains in the locked position shown in FIG. 17, the frame can be removed and reattached to the skull as many times as dictated by the stereotactic radiation therapy.

After completion of the radiation therapy, the lock washer 112 is detached from bushing 102 and the attachment assembly 30 used for another patient. A frame ring 18 and a set of frame arms can be allocated for a single patient over the duration of the radiation treatment or, alternatively, the same ring and arms can be used by multiple patients by readjusting the arms for each patients skull dimensions (see FIG. 5). It is important to identify each arm and record the mounting location for each arm on ring 18 as well as the bore, like bores 46 in FIG. 5, used to mount the arm on the ring. This ensures that the entire frame is accurately reassembled when additional fractionated radiosurgery is to be performed. If multiple patients share the same frame, a set of individual attachment assemblies 30 are maintained for each patient. It is important to note that all clamping, drilling, tapping, insertion, and attachment assemblies reside along a single longitudinal axis. Maintaining a single longitudinal axis ensure that the screw pins attach symmetrically inside the receptor socket and increase frame stability.

Figure 18:
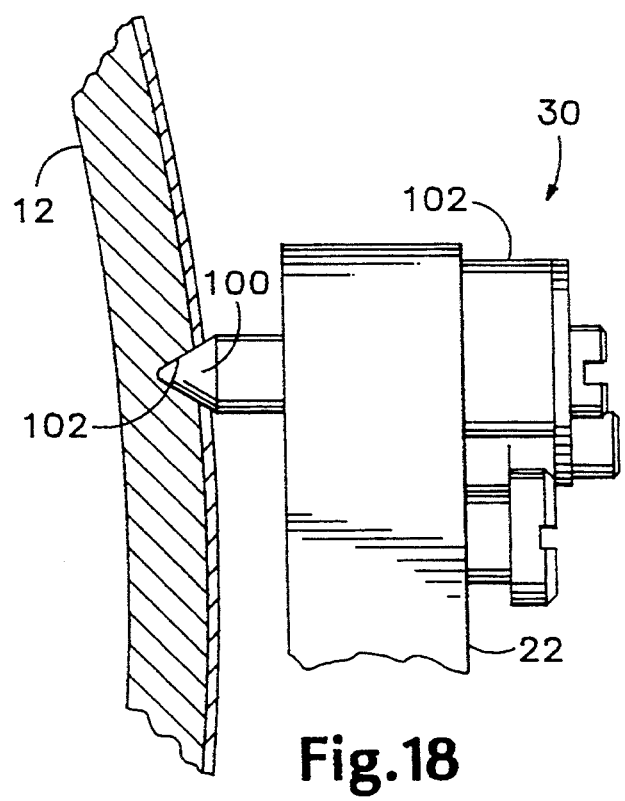
FIG. 18 is a side view of the attachment assembly shown in FIG. 12 inserted directly into a skull hole.

FIG. 18 is a side view of the attachment assembly 30 shown in FIG. 12 inserted directly into a skull hole 120. In another embodiment of the invention, the frame can be attached directly into skull hole 120. The process for attaching the frame to the skull is identical to the process described above except that the drilling procedure (FIG. 9) is performed such that the skull hole 120 is tapered to receive the conical tip 100 of screw pin 95. The tapping and receptor insertion procedures are then no longer required. The lateral coordinates of the frame are preserved by the locked attachment assembly 102, and the longitudinal and latitudinal coordinates of the frame are preserved by the locations of the drilled skull holes 120 that remain in the patient for the entire stereotactic radiation treatment.

The embodiment shown in FIG. 18 leaves a visually less obvious frame receptor in the patient's skull. The direct frame attachment process also requires fewer steps to install the frame and requires fewer assemblies to initially attach the frame to the skull. Various skull hole, drill bit, and screw pin designs can be utilized to perform the steps described above. Alternate assemblies can also be incorporated into the arm holes for other stereotactic radiosurgery procedures. All assembly components are preferably titanium for MRI and CT compatibility except for the arms which are aluminum or plastic.

Receptors imbedded in the skull art: superior to bore cavities bored into the bone surface. Repeated frame/pin attachment requires a relatively hard surface.

The overall process for using the stereotactic frame according to the invention is now described. The frame arms 20, 22, 26, and 28 (FIG. 2) are first adjusted in ring 18 according to the size of the patients skull. The clamp assemblies 52 (FIG. 7) are locked into the arm holes 36 and the clamps attached to the patients skull. After the clamps are tightened to the patients skull, one of the clamp assemblies 52 is removed and replaced with the drill assembly 68 (FIG. 9). A hole is then drilled in the skull along the same axis as previously defined by the clamp assembly 52. After the hole is drilled in the skull, the drill assembly is removed, and if necessary, the tap assembly 78 (FIG. 10) is inserted into the arm hole 36. After the skull hole is tapped, the tap assembly 78 is removed from the arm, and if required, the insertion assembly 84 (FIG. 11) is inserted into the arm. The insertion assembly is used to insert a receptor 32 into the tapped skull hole and then removed from the frame arm. The attachment assembly 30 (FIG. 12) is then installed in the arm and the attachment assembly screw pin 95 inserted into the receptor 32.

The above process is performed for the remaining three arms so that each arm has an associated attachment assembly installed in a receptor (see FIG. 2). Each attachment assembly screw pin 95 is then locked to the associated screw pin bushing 102 with a lock washer 112 and screw 110 as shown in FIG. 15. At this point, the frame 18 is securely attached to the skull and the localization process begins. After the initial localization process and after the first radiation treatment, the frame may be removed from the patient by unscrewing the lock screws 62 and removing each attachment assembly 30 from its arm (FIG. 17). The locked attachment assemblies 30 are labeled and preserved for further treatments on the patient. The patient carries the receptors 32 in his skull throughout the stereotactic radiation therapy.

At each subsequent radiation therapy session, the frame 18 is positioned around the patients head and the locked attachment assemblies 30 reinserted into the associated arm holes 36. The attachment assemblies are then forced into the receptors 32 by lock screw 62. The radiation therapy is then carried out without having to relocalize the target. After completion of the therapy session, the frame 18 is again removed and the attachment assemblies stored for the next radiosurgical session. Thus, fractionated stereotactic radiosurgery may be performed at a reasonable cost.

During the tinges between therapy sessions, receptors 32 remain fixed in the patients skull and extend just above the surface of the skin as shown in FIG. 12. At the conclusion of the fractionated stereotactic radiosurgery according to the present invention, receptors 32 are unscrewed using assembly 84 as shown in FIG. 11. The skin around the former location of the receptor is then closed and treated as necessary to ensure satisfactory healing.

Figure 19:
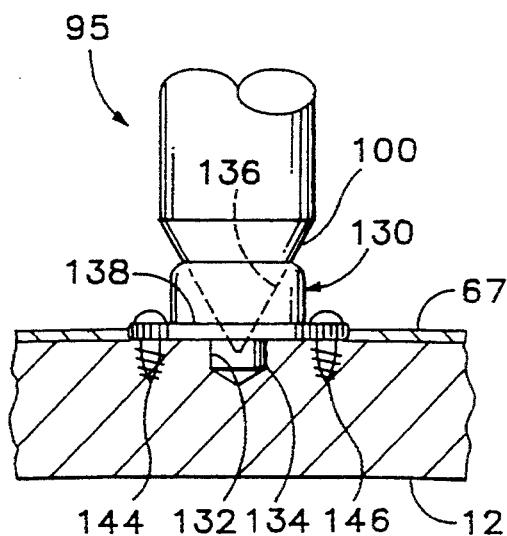
FIG. 19 is a view of an alternate embodiment of a receptor.
Figure 20:
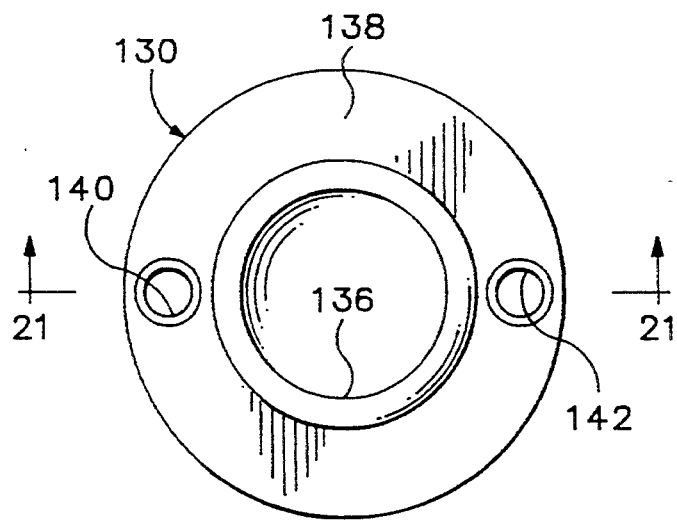
FIG. 20 is an enlarged top view of the receptor of FIG. 19.
Figure 21:
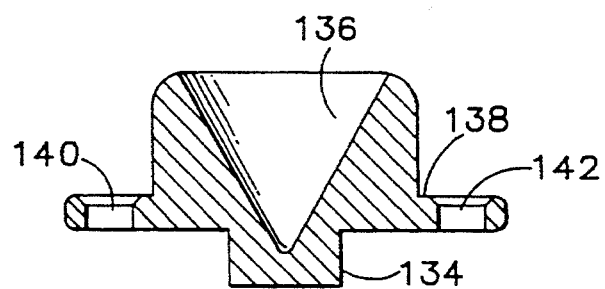
FIG. 21 is a view taken along line 21—21 in FIG. 20.

Turning now to FIG. 19, illustrated therein is another embodiment of a receptor 130 which performs a similar function to receptor 32 in FIG. 12. In the embodiment of FIG. 19 a drill assembly( not shown) similar to drill assembly 68 in FIG. 9 is used to create a bore 132 in skull 12. The drill assembly is connected to frame 18 in the manner previously described and a drill bit (also not shown) which is smaller than drill bit 72 in FIG. 9 is used to create bore 132.

Receptor 130 includes a lug 134 which is received in bore 132. Receptor 130 further includes a conical opening 136 which receives the lower portion of tapered tip 100 as shown in FIG. 19. The perimeter of receptor 130 includes a circular flange 138 having a pair of countersunk holes 140, 142 therethrough.

In use, a bore, like bore 132, is drilled as described above opposite each of the arms in frame 18. Next, a spot of glue is placed on lug 134 and/or in bore 132. When the lug is pressed into the bore, receptor 130 is firmly secured to skull 12 without requiring a larger bore to be drilled in the skull, as described in connection with the embodiment of FIG. 11. In the event the glue is not sufficient to properly secure receptor 130, additional small pilot holes can be drilled in skull 12 through holes 140, 142 in the receptor to permit screws, like screws 144, 146 to be installed to secure the receptor to the skull. After installation, pin 95 is installed with its associated bushing (in FIG. 12) so that tip 100 is received in the receptor as shown in FIG. 19.

Having described anti illustrated the principles of the invention in a preferred embodiment thereof, it should be apparent that the invention can be modified in arrangement and detail without departing from such principles. I claim all modifications and variation coming within the spirit and scope of the following claims:

1. A method for performing stereotactic radiosurgery upon a target within a skull, comprising:
providing a frame including laterally extendable mounting devices for positioning around the skull and mounting receptors for holding the frame;
fastening the mounting receptors to the skull;
attaching the frame to the mounting receptors at a preset position with respect to the skull so that each mounting device extends from the frame in a given laterally extended condition, the preset frame position used as a target reference point for defining a multidimensional coordinate system to precisely identify a target;
locking each mounting device into its associated laterally extended condition;
detaching the frame from the mounting receptors while each mounting device remains locked in said associated laterally extended condition: and
reattaching the frame to the mounting receptors at the preset position during various stages of the stereotactic radiosurgery, the frame after being reattached to the mounting receptors reestablishing the target reference point used to initially identify the target.

2. A method for performing stereotactic radiosurgery upon a target within a skull comprising:
providing a frame for positioning around the skull and mounting receptors for holding the frame;
clamping the rigid frame at given locations on the skull;
drilling holes into the skull at the given locations where the frame is clamped to the skull;
inserting one of said mounting receptors into each skull hole for receiving and holding the frame around the skull;
attaching the frame to the mounting receptors at a preset position with respect to the skull, the preset frame position used as a reference point for defining a multi-dimensional coordinate system to precisely identify a target; and
detaching and reattaching the frame to the mounting receptors at the preset position during various stages of the stereotactic radiosurgery, the frame after being reattached to the mounting receptors reestablishing the same target reference point used to initially identify the target.

3. The method according to claim 2 wherein attaching the frame to the receptors includes positioning the frame at a predetermined location in the receptors and repositioning the frame at that same location every time the frame is reattached to the skull.

4. The method according to claim 2 wherein the frame is initially attached to the skull to determine said reference point for a radiosurgical procedure and removed between each subsequent radiosurgical procedure required during a stereotactic treatment process, the receptors remaining attached to the skull during the stereotactic treatment process for providing a reproducible reference point for the frame.

5. A method for performing high precision stereotactic radiosurgery on a lesion in a skull, comprising:
mounting a frame to the skull, the frame defining a multi-dimensional coordinate system used as a reference for a first stereotactic radiosurgical procedure;
drilling holes into the skull at locations where the frame is mounted to said skull;
installing receptors into the skull holes;
attaching the frame to the receptors thereby locating said frame about the skull at a given reference position;
localizing the lesion according to the frame reference position;

performing the first stereotactic radiosurgical procedure;

detaching the frame after the first stereotactic radiosurgical procedure, the receptors remaining installed in the skull holes;

reattaching the frame to the receptors; and performing a second stereotactic radiosurgical procedure, the frame being relocated in the same reference position in the receptors.

6. The method of claim 5 wherein the step of localizing the lesion includes the step of deriving a set of lesion coordinates relative to the frame reference position.

7. The method of claim 6 wherein each radiosurgical procedure is performed using the same lesion coordinates.

* * * * *